US010973726B2

(12) United States Patent
Choi et al.

(10) Patent No.: US 10,973,726 B2
(45) Date of Patent: Apr. 13, 2021

(54) MOTION ASSISTANCE APPARATUS

(71) Applicants: Samsung Electronics Co., Ltd., Suwon-si (KR); Korea University of Technology and Education Industry-University Cooperation Foundation, Cheonan-si (KR)

(72) Inventors: Byungjune Choi, Gunpo-si (KR); Youn Baek Lee, Yongin-si (KR); Youngbo Shim, Seoul (KR); Yong Jae Kim, Cheonan-si (KR)

(73) Assignees: Samsung Electronics Co., Ltd, Gyeonggi-do (KR); Korea University of Technology and Education Industry-University Cooperation Foundation, Chungcheongnam-do (KR)

( * ) Notice: Subject to any disclaimer, the term of this patent is extended or adjusted under 35 U.S.C. 154(b) by 305 days.

(21) Appl. No.: 15/871,455

(22) Filed: Jan. 15, 2018

(65) Prior Publication Data

US 2019/0070061 A1  Mar. 7, 2019

(30) Foreign Application Priority Data

Sep. 4, 2017 (KR) .................. 10-2017-0112647

(51) Int. Cl.
*A61F 5/01* (2006.01)
*A61H 3/00* (2006.01)
(Continued)

(52) U.S. Cl.
CPC ............... *A61H 3/00* (2013.01); *A61F 2/64* (2013.01); *A61F 5/0123* (2013.01); *A61H 1/024* (2013.01); *A61F 2002/5067* (2013.01); *A61F 2002/6836* (2013.01); *A61F 2005/0139* (2013.01); *A61F 2005/0141* (2013.01); *A61F 2005/0144* (2013.01); *A61F 2005/0146* (2013.01); *A61F 2005/0155* (2013.01);
(Continued)

(58) Field of Classification Search
CPC ...... A61F 2005/0146; A61F 2005/0155; A61F 2002/5084; B25J 9/0006
See application file for complete search history.

(56) References Cited

U.S. PATENT DOCUMENTS 5,472,412 A    12/1995  Knoth
2012/0330198 A1  12/2012  Patoglu
(Continued)

FOREIGN PATENT DOCUMENTS

EP    1 260 201 A1    11/2002
EP    2 923 804 A1    9/2015
(Continued)

OTHER PUBLICATIONS

Extended European Search Report issued by the European Patent Office dated Jan. 22, 2019 for corresponding EP Application No. 18181733.9.

*Primary Examiner* — David H Willse
(74) *Attorney, Agent, or Firm* — Harness, Dickey and Pierce, P.L.C.

(57) ABSTRACT

A motion assistance apparatus including a proximal frame configured to support a proximal part of a user, a distal frame configured to support a distal part of the user, and a force transmitting member slidably connected to the proximal frame, and rotatably connected to the distal frame is provided.

20 Claims, 16 Drawing Sheets

(51) Int. Cl.
*A61F 2/64* (2006.01)
*A61H 1/02* (2006.01)
A61F 2/50 (2006.01)
A61F 2/68 (2006.01)

(52) U.S. Cl.
CPC .......................... *A61F 2005/0158* (2013.01); *A61H 2003/007* (2013.01); *A61H 2201/0192* (2013.01); *A61H 2201/1207* (2013.01); *A61H 2201/1215* (2013.01); *A61H 2201/149* (2013.01); *A61H 2201/1436* (2013.01); *A61H 2201/164* (2013.01); *A61H 2201/165* (2013.01); *A61H 2201/1666* (2013.01); *A61H 2201/1676* (2013.01); *A61H 2205/102* (2013.01)

(56) References Cited

U.S. PATENT DOCUMENTS

| | | |
|---|---|---|
| 2015/0051527 A1 | 2/2015 | Potter et al. |
| 2016/0158087 A1 | 6/2016 | Huang et al. |
| 2016/0184111 A1 | 6/2016 | Ikedo et al. |
| 2016/0374888 A1 | 12/2016 | Tung et al. |

FOREIGN PATENT DOCUMENTS

| | | | |
|---|---|---|---|
| KR | 101242517 B | 3/2013 | |
| KR | 101666202 B | 10/2016 | |
| KR | 1020170021018 A | 2/2017 | |
| WO | WO 94/18916 A1 * | 9/1994 | ............... A61F 5/01 |
| WO | WO-2012/070244 A1 | 5/2012 | |

* cited by examiner

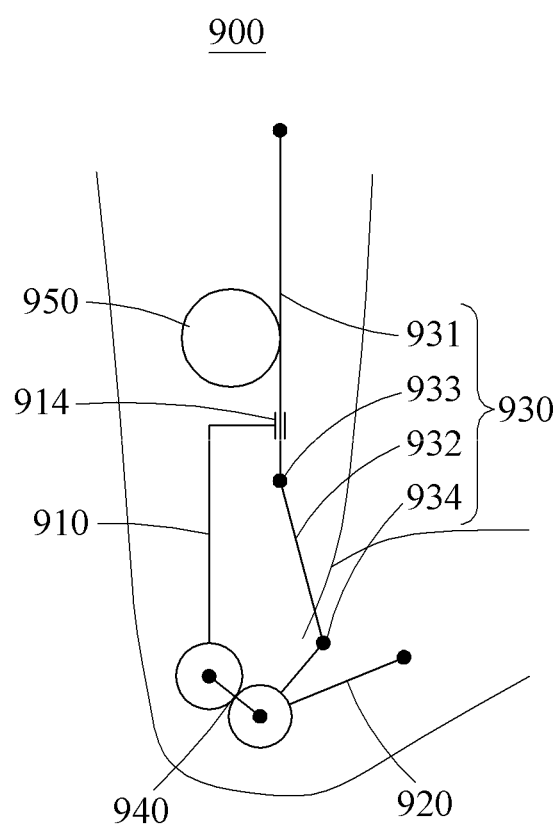

MOTION ASSISTANCE APPARATUS

CROSS-REFERENCE TO RELATED APPLICATION

This application claims priority under 35 U.S.C. § 119 to Korean Patent Application No. 10-2017-0112647, filed on Sep. 4, 2017, in the Korean Intellectual Property Office, the entire contents of which are incorporated herein by reference in their entirety.

BACKGROUND

1. Field

At least one example embodiment relates to a motion assistance apparatus.

2. Description of the Related Art

With the onset of rapidly aging societies, an increasing number of people may experience inconvenience and/or pain from joint problems. Thus, there may be a growing interest in motion assistance apparatuses enabling the elderly and/or patients having joint problems to walk with less effort.

SUMMARY

Some example embodiments relate to a motion assistance apparatus.

In some example embodiment, the motion assistance apparatus may include a motion assistance apparatus.

In some example embodiments, the motion assistance apparatus may include a proximal frame configured to support a proximal part of a user; a distal frame configured to support a distal part of the user; and a force transmitter slidably connected to the proximal frame, and rotatably connected to the distal frame.

In some example embodiments, the motion assistance apparatus may include a connector configured to resist separation of the distal frame from the proximal frame such that the distal frame rotates while being in rolling contact with the proximal frame.

In some example embodiments, the distal frame is configured to perform a 2-degree of freedom (DOF) motion with respect to the proximal frame, the 2-DOF motion including a motion in a direction that traverses a sagittal plane of the user.

In some example embodiments, one or more of the proximal frame and the distal frame comprises: two segment frames; and a joint configured to connect the two segment frames such that a first one of the two segment frames rotates with respect to a second one of the two segment frames in a direction that traverses the sagittal plane of the user.

In some example embodiments, the proximal frame includes two proximal segment frames, and a first joint configured to connect the two proximal segment frames, and the distal frame includes two distal segment frames, and a second joint configured to connect the two distal segment frames.

In some example embodiments, the motion assistance apparatus further includes a joint fixer configured to fix one of the first joint and the second joint.

In some example embodiments, the joint is configured to have an axis that inclines such that the joint of the motion assistance apparatus is close to a joint of the user connecting the proximal part and the distal part of the user in a direction from a rear side of the user toward a front side of the user when the joint of the motion assistance apparatus fully extends.

In some example embodiments, the proximal frame includes a guide configured to guide a movement of the force transmitter, the force transmitter including, a slider configured to move along the guide; and a pusher having a first end and a second end, the first end and the second end of the pusher rotatably connected to the slider and the distal frame, respectively.

In some example embodiments, the force transmitter further includes a first connector configured to connect the slider and the pusher; and a second connector configured to connect the pusher and the distal frame, the first connector and the second connector each being one of a universal joint and a ball joint.

In some example embodiments, the slider is configured to slide between a first position and a second position, the second position being closer to the distal frame than the first position such that an angle between the proximal frame and the distal frame decreases as the slider slides from the first position toward the second position.

In some example embodiments, a shape of the pusher is convex in a direction away from the proximal frame when the proximal frame and the distal frame fully extend.

In some example embodiments, the motion assistance apparatus further includes a rotary body rotatably connected to the proximal frame; and a wire configured to connect the rotary body and the slider.

In some example embodiments, first and second ends of the wire are fixed to first and second sides of the slider, respectively, and a middle portion of the wire is configured to wind over the rotary body at least one time.

In some example embodiments, the motion assistance apparatus further includes a tension adjusting piece configured to move with respect to the rotary body, the tension adjusting piece having a portion of the wire fixed thereto.

In some example embodiments, the motion assistance apparatus includes a pinion gear rotatably connected to the proximal frame, and wherein the slider includes a rack gear configured to engage with the pinion gear.

In some example embodiments, the distal frame includes a side frame connected to the proximal frame; and a front frame configured to adjust a position thereof with respect to the side frame, and to enclose a front surface of the distal part.

Some other example embodiments also relate to a motion assistance apparatus.

In some example embodiments, the motion assistance apparatus includes a shank frame configured to support a shank of a user; and a thigh frame connected to the shank frame, the thigh frame configured to rotate in a first direction, the thigh frame including a joint configured to rotate the shank frame in a second direction that traverses a sagittal plane of the user, the second direction differing from the first direction.

In some example embodiments, the joint of the thigh frame is above a knee of the user when the user is wearing the motion assistance apparatus.

In some example embodiments, the shank frame includes a joint below a knee of the user when the user is wearing the motion assistance apparatus, the joint of the shank frame being fixed and configured to deform the shank frame such that the shank frame is in close contact with the user.

In some example embodiments, includes a force transmitter slidably and rotatably connected to the thigh frame, and rotatably connected to the shank frame.

In some example embodiments, a rotation axis of the joint of the thigh frame inclines downward in a direction toward a front side of the user when the user is wearing the motion assistance apparatus.

In some example embodiments, the joint of the thigh frame inclines downward at an angle, the angle being between 20 degrees and 70 degrees.

Some other example embodiments also relate to a motion assistance apparatus configured to assist a user.

In some example embodiments, the motion assistance apparatus includes a connector configured to connect a first frame and a second frame such that the second frame is configured to rotate with respect to the first frame while remaining in rolling contact with the first frame.

In some example embodiments, the first frame includes two first segment frames connected via a first joint, the first joint configured to act as a passive joint such that the first joint enables the second frame to rotate with respect to the first frame in a direction traverse to a sagittal plane of the user, and the second frame includes two second segment frames connected via a second joint, the second joint configured to act as a fixed joint such that the second frame remains in alignment with a joint of the user while the user is walking.

In some example embodiments, the motion assistance apparatus includes a rotary body and a force transmitter, the force transmitter including a slider, the rotary body and the slider configured to convert rotational power generated by an actuator to rectilinear power, and the force transmitter configured to transmit the rectilinear power to the second frame.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 11B illustrates a motion assistance apparatus being in a flexion state according to at least one example embodiment.

DETAILED DESCRIPTION

Figure 1:
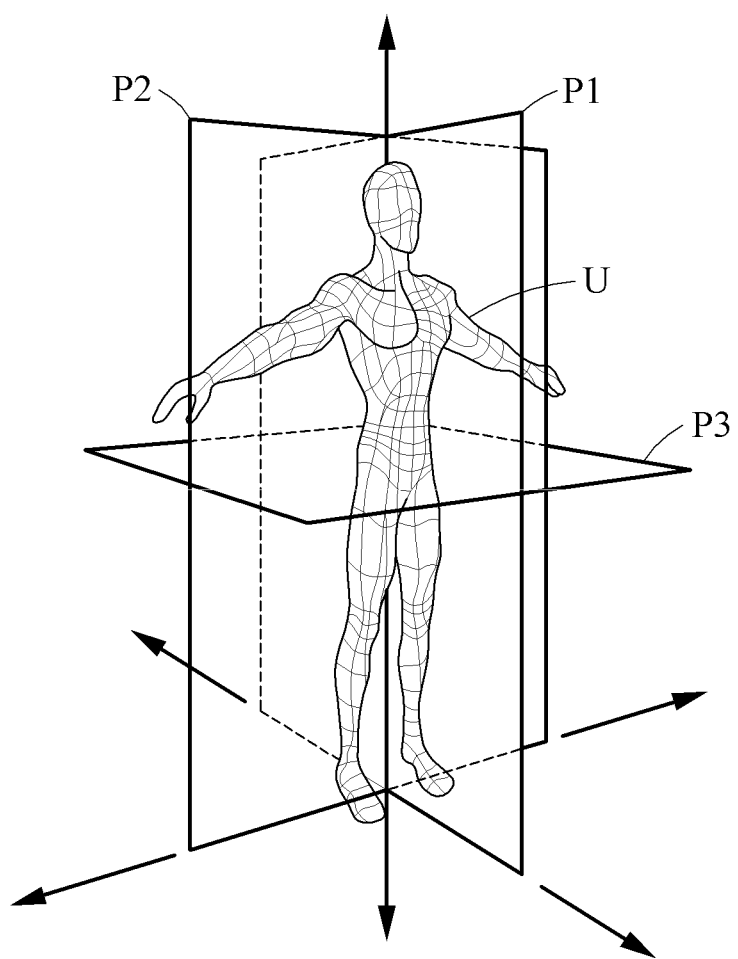
FIG. 1 illustrates a sagittal plane, a frontal plane, and a transverse plane of a user according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

FIG. 1 illustrates a sagittal plane, a frontal plane, and a transverse plane of a user according to at least one example embodiment.

Referring to FIG. 1, a sagittal plane P1 is a plane that divides a user U into right and left portions, a frontal plane P2 is a plane that divides the user U into anterior and posterior portions, and a transverse plane P3 is a plane that divides the user U into upper and lower portions. A motion of the user U may be construed as being performed on the three planes P1, P2, and P3. For example, when the user U performs a flexion motion or an extension motion of a leg, a shank of the user U may rotate with respect to a thigh on the sagittal plane P1, and also rotate in a direction that traverses the sagittal plane P1 (refer to FIGS. 4A and 4B). Hereinafter, a motion of a motion assistance apparatus according to at least one example embodiment will be described based on the sagittal plane P1, the frontal plane P2, and the transverse plane P3.

Figure 2:
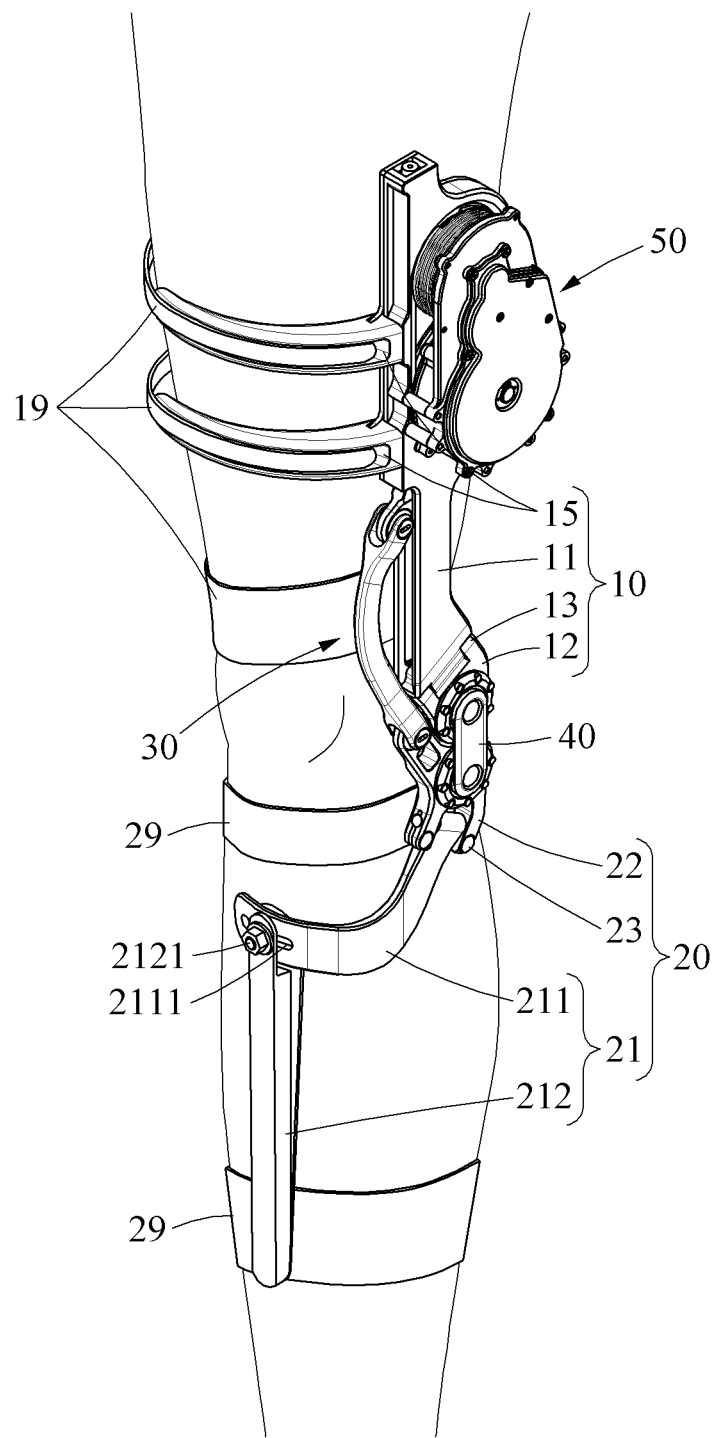
FIG. 2 illustrates a user wearing a motion assistance apparatus according to at least one example embodiment.
Figure 3A:
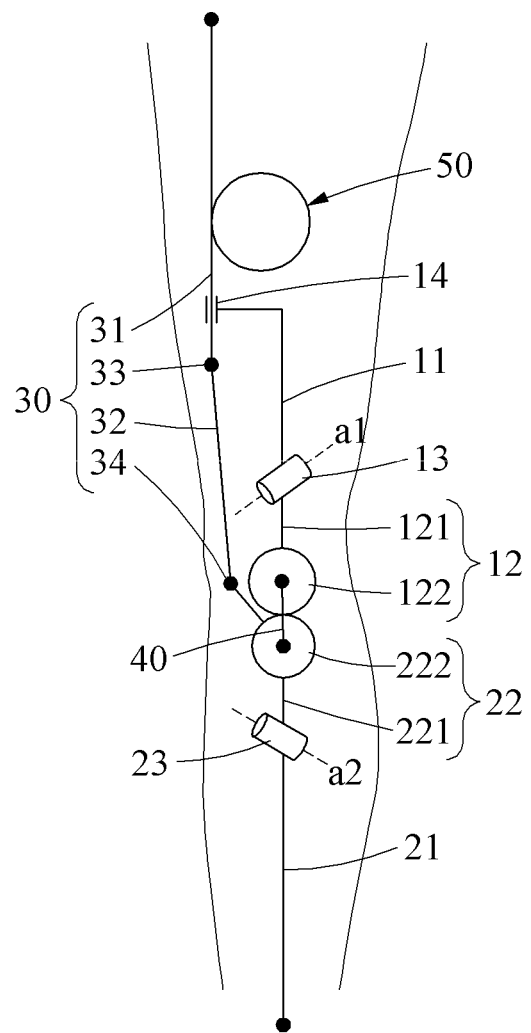
FIG. 3A illustrates a motion assistance apparatus being in an extension state according to at least one example embodiment.
Figure 3B:
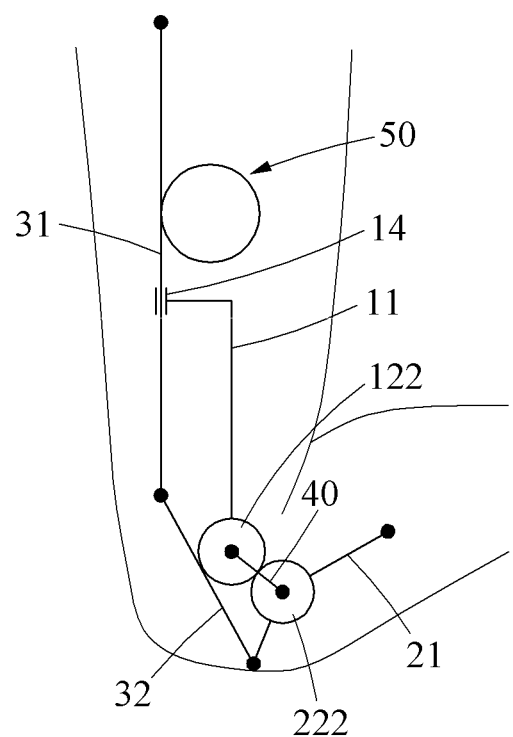
FIG. 3B illustrates a motion assistance apparatus being in a flexion state according to at least one example embodiment.
Figure 4A:
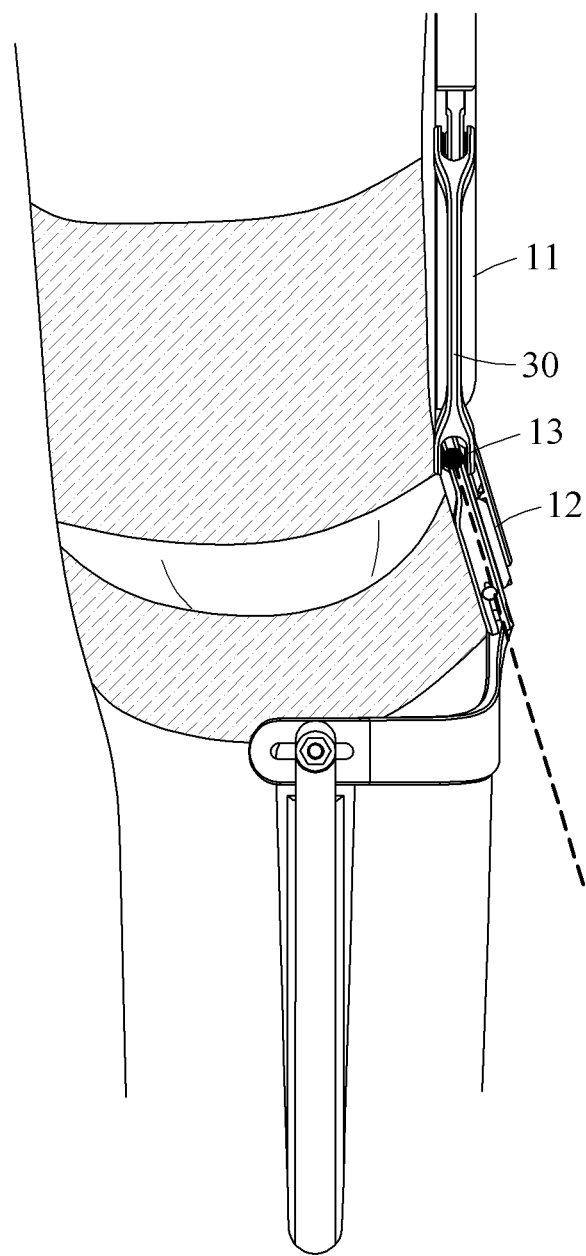
FIG. 4A illustrates a knee joint of a user wearing a motion assistance apparatus, the knee joint being in an extension state according to at least one example embodiment.
Figure 4B:
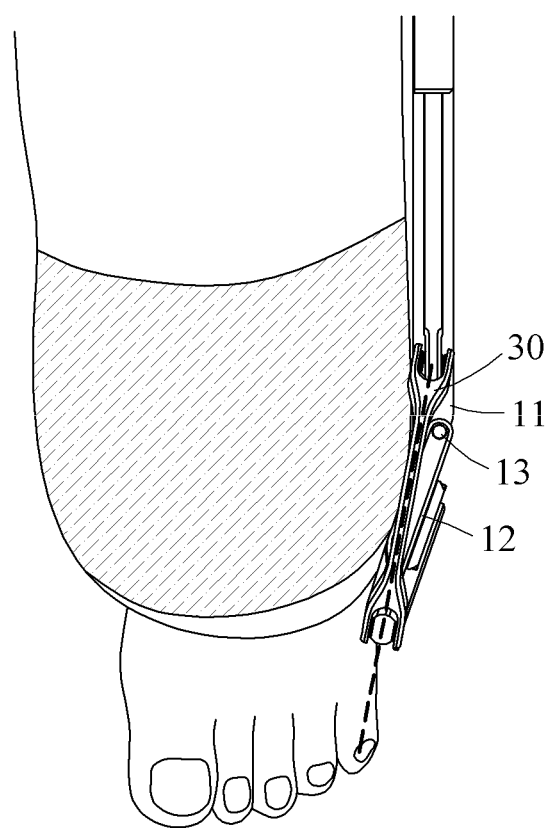
FIG. 4B illustrates a knee joint of a user wearing a motion assistance apparatus, the knee joint being in a flexion state according to at least one example embodiment.
Figure 5:
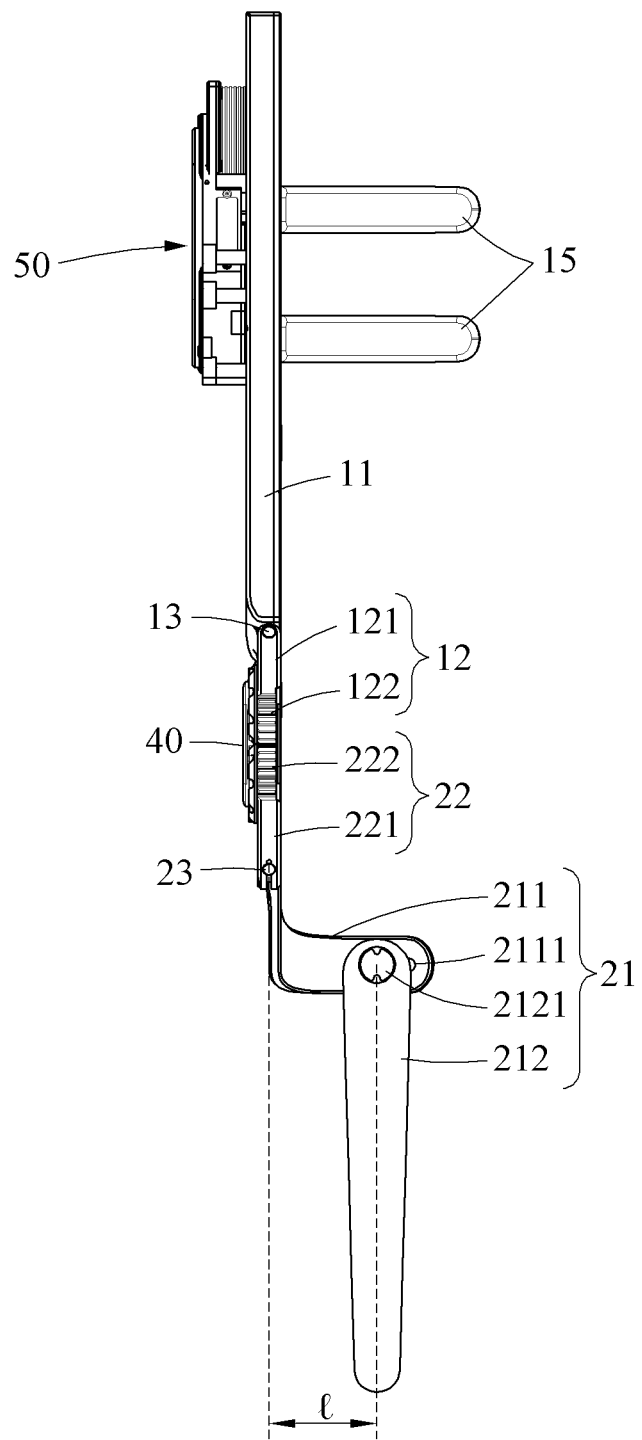
FIG. 5 is a rear view illustrating a motion assistance apparatus according to at least one example embodiment.

FIG. 2 illustrates a user wearing a motion assistance apparatus according to at least one example embodiment. FIG. 3A illustrates the motion assistance apparatus being in an extension state according to at least one example embodiment, and FIG. 3B illustrates the motion assistance apparatus being in a flexion state according to at least one example embodiment. FIG. 4A illustrates a knee joint of the user wearing the motion assistance apparatus, the knee joint being in an extension state, while viewing the standing user from a front, according to at least one example embodiment. FIG. 4B illustrates the knee joint of the user wearing the motion assistance apparatus, the knee joint being in a flexion state, while viewing the sitting user from a top, according to at least one example embodiment. FIG. 5 is a rear view illustrating the motion assistance apparatus according to at least one example embodiment.

Referring to FIGS. 2 through 5, a motion assistance apparatus 100 may be worn by a user to assist a motion of the user. The user may correspond to a human, an animal, or a robot. However, the user is not limited thereto. The motion assistance apparatus 100 may include a proximal frame 10, a distal frame 20, a force transmitting member 30, a connecting member 40, and an actuator 50.

The proximal frame 10 and the distal frame 20 may be on opposite sides of a part of the user to support a proximal part and a distal part of the user, respectively. For example, the proximal frame 10 and the distal frame 20 may be on opposite sides of a knee of the user. The proximal frame 10 may support a part of the user above the knee, for example, a thigh of the user, and the distal frame 20 may support a part of the user below the knee, for example, a shank and/or a calf of the user. The proximal frame 10 may be a thigh frame, and may include a detachable proximal belt 19 configured to enclose a circumference of the thigh of the user. Similarly, the distal frame 20 may be a shank frame, and may include a detachable distal belt 29 configured to enclose a circumference of the shank and the calf of the user. A plurality of detachable proximal belts 19 may be provided in a longitudinal direction of the proximal frame 10, and a plurality of detachable distal belts 29 may be provided in a longitudinal direction of the distal frame 20. A circumference of the detachable proximal belt 19 and/or a circumference of the detachable distal belt 29 may be adjustable to be suitable for a body of the user. For example, the detachable proximal belt 19 and/or the detachable distal belt 29 may include a hook and loop fastener structure.

In another example embodiment, the proximal frame 10 and the distal frame 20 may be on opposite sides of an elbow joint of the user. The proximal frame 10 may support a shoulder and/or a back, and the distal frame 20 may support a forearm. The proximal frame 10 may include a detachable belt configured to support the entire shoulder of the user, and the distal frame 20 may include a detachable belt configured to support the entire forearm of the user or a structure that encloses the entire forearm. Hereinafter, the description will be provided based on a case in which the proximal frame 10 and the distal frame 20 are on opposite sides of the knee of the user. However, at least one example embodiment is not limited thereto.

The proximal frame 10 may include a first proximal segment frame 11, a second proximal segment frame 12, a first joint 13, a guide 14, and a proximal support frame 15.

The first proximal segment frame 11 may support a side of the proximal part of the user. The first proximal segment frame 11 may be a longitudinal member configured to support a side of the thigh of the user. When the user wears the motion assistance apparatus 100, a longitudinal direction of the first proximal segment frame 11 may be parallel to a longitudinal direction of the proximal part of the user, for example, the thigh of the user.

The second proximal segment frame 12 may support a side of a joint connecting the proximal part and the distal part of the user. In a case in which the proximal frame 10 supports the thigh of the user and the distal frame 20 supports the shank of the user, the second proximal segment frame 12 may support a side of the knee of the user. The second proximal segment frame 12 may be rotatably connected to one end of the first proximal segment frame 11.

The first joint 13 may be positioned above the knee of the user, and rotatably connect the first proximal segment frame 11 and the second proximal segment frame 12 in a direction that traverses a sagittal plane. The first joint 13 may connect one end of the first proximal segment frame 11 and one end of the second proximal segment frame 12. For example, the first joint 13 may be a hinge including a pin to be inserted into the first proximal segment frame 11 and the second proximal segment frame 12. The first joint 13 may be construed as a bending element or a pivotally connected element.

The first proximal segment frame 11 and the second proximal segment frame 12 may relatively rotate on the first joint 13, thereby providing a degree of freedom (DOF) for the distal frame 20 supporting the shank of the user to move with respect to the proximal frame 10 supporting the thigh of the user in a direction that traverses the sagittal plane. In reality, the thigh and the shank of the user may move in a direction parallel to the sagittal plane and in a direction that traverses the sagittal plane during the extension motion and the flexion motion. Thus, the above structure may be used to improve a user wearability. In detail, as a knee joint of the user being bent at 90 degrees moves to be in an extension state at 0 degrees, an angle of the shank with respect to the thigh which is projected on a frontal plane including the thigh may increase by about −10 degrees to 20 degrees. The first joint 13 of the motion assistance apparatus 100 may adapt to such a change in the angle, and thus the user wearability may improve. Further, the motion assistance apparatus 100 having the structure as described above may operate adaptively to various postures of the user wearing the motion assistance apparatus 100, including a posture of sitting with legs crossed.

An axis a1 of the first joint 13 may incline to be close to a joint connecting the proximal part and the distal part of the user in a direction from a rear side toward a front side of the user when the joint fully extends. For example, in a case in which the joint connecting the proximal part and the distal part of the user is the knee joint, the axis a1 of the first joint 13 may incline to be close to the knee joint of the user in a direction toward the front side of the user. In the example of FIG. 3A, the axis a1 of the first joint 13 may incline downward in a direction toward the front side of the user, for example, at 20 degrees to 70 degrees. The inclining structure may implement a motion more similar to a motion of the knee joint of the user, when compared to a structure in which the axis a1 of the first joint 13 is disposed in a direction perpendicular to the frontal plane. Thus, the user wearability may improve.

The second proximal segment frame 12 may rotate on the first joint 13 with respect to the first proximal segment frame 11, thereby moving in a direction that traverses the sagittal plane of the user. An angle between the first proximal segment frame 11 and the second proximal segment frame 12 may change as the knee joint of the user performs a flexion or extension motion. For example, FIGS. 4A and 4B illustrate the angle between the first proximal segment frame 11 and the second proximal segment frame 12 changing as the knee joint of the user switches from an extension state of FIG. 4A to a flexion state of FIG. 4B. The second proximal segment frame 12 may rotate on the first joint 13 in a direction that traverses an inner side of the user, that is, the sagittal plane of the user, during the flexion motion of the knee joint of the user.

The guide 14 may assist a sliding motion of the force transmitting member 30 in a longitudinal direction of the proximal frame 10. For example, the guide 14 may include a groove that encloses a portion of the force transmitting member 30, and barriers at a front end and a rear end of the groove. In the above structure, the guide 14 may restrict a moving range of the force transmitting member 30, thereby preventing a hyperextension of the joint of the user or an excessive flexional force to be applied to the joint of the user, and thus improving a safety of the motion assistance apparatus 100.

The proximal support frame 15 may protrude from one side of the first proximal segment frame 11. The proximal support frame 15 protruding while forming a desired (or, alternatively, a predetermined) angle with the first proximal segment frame 11 supporting the side of the user may support a front surface of the user. The proximal support frame 15 may have a curved shape, for example, a shape that encloses a portion of the thigh of the user, to increase a contact area with the proximal part of the user. A plurality of proximal support frames 15 may be provided to be spaced apart from each other in a longitudinal direction of the proximal part of the user.

The distal frame 20 may include a first distal segment frame 21, a second distal segment frame 22, and a second joint 23.

The first distal segment frame 21 may support the distal part of the user, for example, the shank of the user. The first distal segment frame 21 may include a side frame 211 configured to support a side of the distal part of the user, and a front frame 212 configured to support a front side of the distal part of the user.

The side frame 211 may have a curved shape. A portion of the side frame 211 may support the side of the distal part of the user, and a remaining portion of the side frame 211 may be curved to have a desired (or, alternatively, a predetermined) angle with respect to the side supporting portion so as to be on the front side of the distal part of the user. For example, when the user wears the motion assistance apparatus 100, the portion of the side frame 211 may support a side of the shank of the user, and the remaining portion of the side frame 211 may cover a front side of the shank of the user.

The front frame 212 may be connected to a portion of the side frame 211, for example, the portion that covers the front side of the shank of the user. The front frame 212 may be a member that is disposed parallel to a longitudinal direction of the shank to support the front side of the shank when the user wears the motion assistance apparatus 100.

The front frame 212 may be installed to be position-adjustable with respect to the side frame 211. For example, the side frame 211 may include a position adjusting slot 2111, and the front frame 212 may include a position fixing member 2121 configured to move and be fixed in the position adjusting slot 2111. The position fixing member 2121 may have a structure in which a male screw and a female screw are combined. The user may move the front frame 212 with respect to the side frame 211 by disassembling the position fixing member 2121.

Referring to FIG. 5, a distance 1 from one side of the side frame 211 to a central axis of the front frame 212 may be adjustable. In the adjustable structure, the front frame 212 may be positioned at a center of the front side of the distal part of the user. Thus, by preventing a dispersion of a force provided to the distal part of the user in an undesired (or, alternatively, a unnecessary) direction, a force transmission efficiency may improve.

The second distal segment frame 22 may support the side of the joint connecting the proximal part and the distal part of the user. For example, in a case in which the proximal frame 10 supports the thigh of the user and the distal frame 20 supports the shank of the user, the second distal segment frame 22 may support the side of the knee of the user. The second distal segment frame 22 may be rotatably connected to one end of the first distal segment frame 21.

The second joint 23 may connect the first distal segment frame 21 and the second distal segment frame 22 to rotate in a direction that traverses the sagittal plane. The second joint 23 may connect one end of the first distal segment frame 21 and one end of the second distal segment frame 22. In the example of FIG. 3A, an axis a2 of the second joint 23 may incline upward in a direction toward the front side of the user, for example, at 20 degrees to 70 degrees. For example, the second joint 23 may be a hinge including a pin to penetrate through the first distal segment frame 21 and the second distal segment frame 22. The first distal segment frame 21 and the second distal segment frame 22 may relatively rotate on the second joint 23, thereby providing a DOF for the distal frame 20 supporting the shank of the user to move with respect to the proximal frame 10 supporting the thigh of the user in a direction that traverses the sagittal plane. Unless otherwise described, the description of the first joint 13 may apply to the second joint 23, and thus duplicated description will be omitted for conciseness.

Meanwhile, one of the first joint 13 and the second joint 23 may be fixed, and the other one of the first joint 13 and the second joint 23 may not be fixed to function as a passive joint. For example, the first joint 13 may not be fixed, and the second joint 23 may be fixed. In this example, the first joint 13 may provide a DOF for the distal frame 20 to rotate with respect to the proximal frame 10 in a direction that traverses the sagittal plane, and the second joint 23 may enable the distal frame 20 to be in close contact with the calf of the user while being fixed. For example, the second joint 23 may be fixed when the distal frame 20 is sufficiently in close contact with the calf of the user by rotating the first distal segment frame 21 while the second joint 23 is not fixed. Thus, irrespective of a thickness of the calf of the user, a space between the user and the motion assistance apparatus 100 may be sufficiently reduced, whereby the user wearability may improve and a protruding height of the entire motion assistance apparatus 100 from the user may be reduced.

That is, the second joint 23 may rotate in response to a motion of the user, and may also be fixed. For example, the second joint 23 may rotate during a process of adjusting the motion assistance apparatus 100 to be in close contact with the body of the user, and may be fixed when the motion assistance apparatus 100 is in close contact with the body of the user.

The second proximal segment frame 12 of the proximal frame 10 and the second distal segment frame 22 of the distal frame 20 may be connected to relatively rotate. The second proximal segment frame 12 and the second distal segment frame 22 may rotate while being in rolling contact with each other. The rolling contact may include a rolling contact in which a plurality of gears rotates while engaging with each other, or a rolling contact in which a plurality of pulleys rotate with respect to each other by a frictional force. For example, the second proximal segment frame 12 and the second distal segment frame 22 may have toothed shapes to engage with each other.

The second proximal segment frame 12 may include a proximal gear 122 fixed to a proximal body frame 121, and the second distal segment frame 22 may include a distal gear 222 fixed to a distal body frame 221 to rotate while engaging with the proximal gear 122. Meanwhile, the proximal frame 10 and the distal frame 20 may rotate using a scheme other than the rolling contact. For example, the proximal frame 10 and the distal frame 20 may be connected to rotate on a single joint.

The connecting member 40 may connect the proximal frame 10 and the distal frame 20 such that the distal frame 20 may rotate while being in rolling contact with the proximal frame 10. The connecting member 40 may be a member configured to connect a central axis of the proximal gear 122 and a central axis of the distal gear 222, and maintain a desired (or, alternatively, a predetermined) distance therebetween.

In the above structure, the distal frame 20 may perform an at least 2-DOF motion with respect to the proximal frame 10. The distal frame 20 may rotate while being in rolling contact with the proximal frame 10, thereby rotating on the sagittal plane of the user. Further, the distal frame 20 may rotate with respect to the proximal frame 10 on the first joint 13 and/or the second joint 23 in a direction that traverses the sagittal plane of the user.

The force transmitting member 30 may transmit a power generated by the actuator 50 to the distal frame 20. The force transmitting member 30 may include a slider 31, a pusher 32, a first connector 33, and a second connector 34. For example, the force transmitting member 30 may be positioned on a side of the leg of the user. When viewing the user wearing the motion assistance apparatus 100 from the side, the force transmitting member 30 may be positioned on a front side from a central line of the thigh of the user.

The slider 31 may slide along the guide 14 on one side of the proximal frame 10. One end of the pusher 32 may be rotatably connected to the slider 31, and another end of the pusher 32 may be rotatably connected to the distal frame 20. The first connector 33 may connect the slider 31 and the pusher 32 such that the pusher 32 may perform an at least 2-DOF rotation with respect to the slider 31. Similarly, the second connector 34 may also connect the pusher 32 and the distal frame 20 such that the distal frame 20 may perform an at least 2-DOF rotation with respect to the pusher 32. For example, the first connector 33 and the second connector 34 may each be a universal joint or a ball joint. By the above structure of the connectors, although the distal frame 20 rotates with respect to the proximal frame 10 in a direction that traverses the sagittal plane, the pusher 32 may effectively transmit a force to the distal frame 20.

The actuator 50 may generate a power to drive the force transmitting member 30. The actuator 50 may generate the power to drive the force transmitting member 30 using a voltage, a current, and/or a hydraulic pressure. The actuator 50 may be arranged to be close to the proximal part of the user which is away from the knee joint of the user receiving an assistance force, as shown in FIGS. 3A and 3B. The above arrangement may reduce a moving radius of the actuator 50 while the user is performing a walking motion, when compared to a case in which the actuator 50 is arranged on the knee of the user. Thus, an influence of an inertial moment by the relatively heavy actuator 50 may be reduced, and an energy efficiency of the motion assistance apparatus 100 may improve.

The motion assistance apparatus 100 may further include a controller (not shown) that includes a processor and a memory. The memory may contain computer readable instructions executable by the processor to control the actuator 50 to drive the force transmitting member 30 to perform an extension motion and/or a flexion motion.

The extension motion and the flexion motion by the motion assistance apparatus 100 will be described with reference to FIGS. 3A and 3B. When the motion assistance apparatus 100 switches from an extension state to a flexion state, an angle between the slider 31 and the pusher 32 and an angle between the pusher 32 and the distal frame 20, projected on the sagittal plane, may decrease and the flexion motion of the user may be assisted. Conversely, when the motion assistance apparatus 100 switches from the flexion state to the extension state, the angle between the slider 31 and the pusher 32 and the angle between the pusher 32 and the distal frame 20, projected on the sagittal plane, may increase and the extension motion of the user may be assisted.

Figure 6:
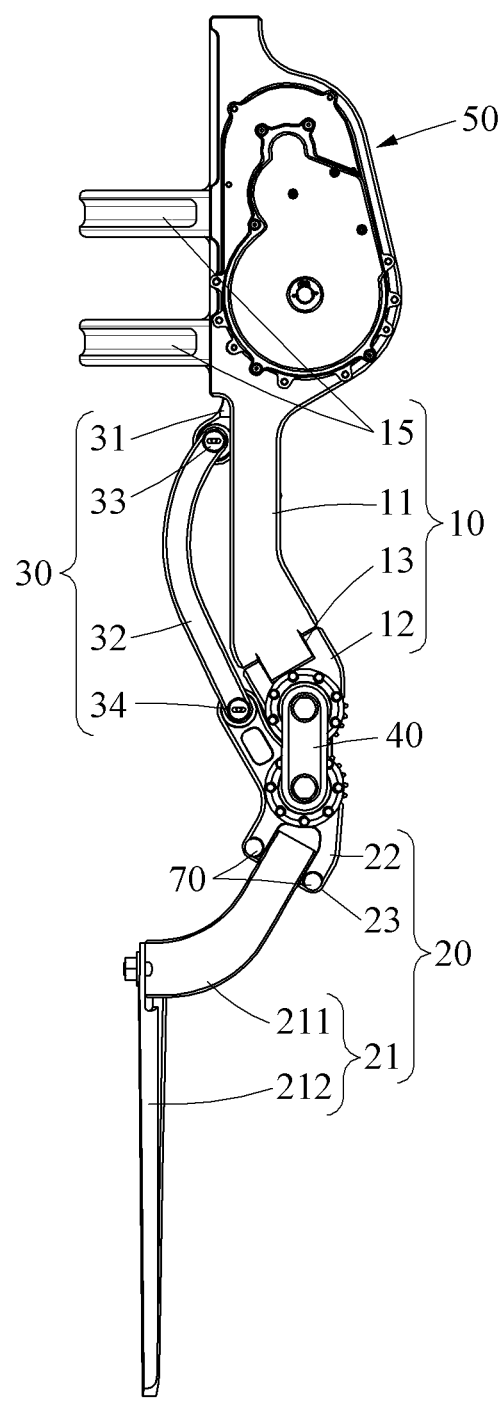
FIG. 6 is a left side view illustrating a motion assistance apparatus being in an extension state according to at least one example embodiment.
Figure 7:
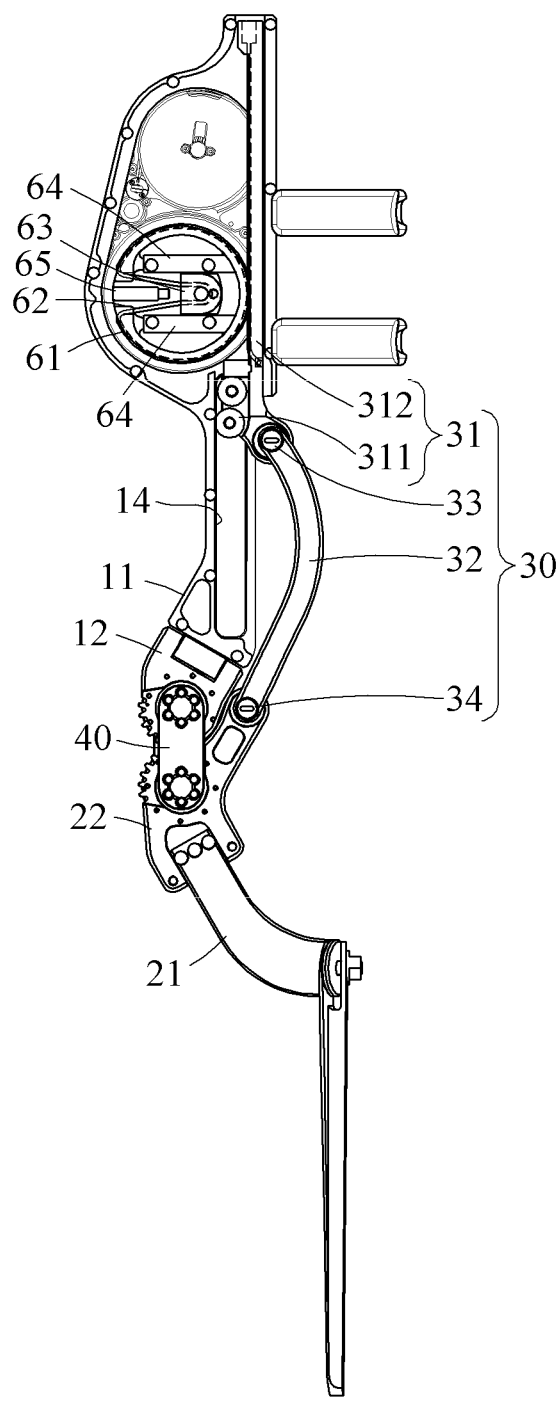
FIG. 7 is a right side view illustrating a motion assistance apparatus being in an extension state according to at least one example embodiment.
Figure 8:
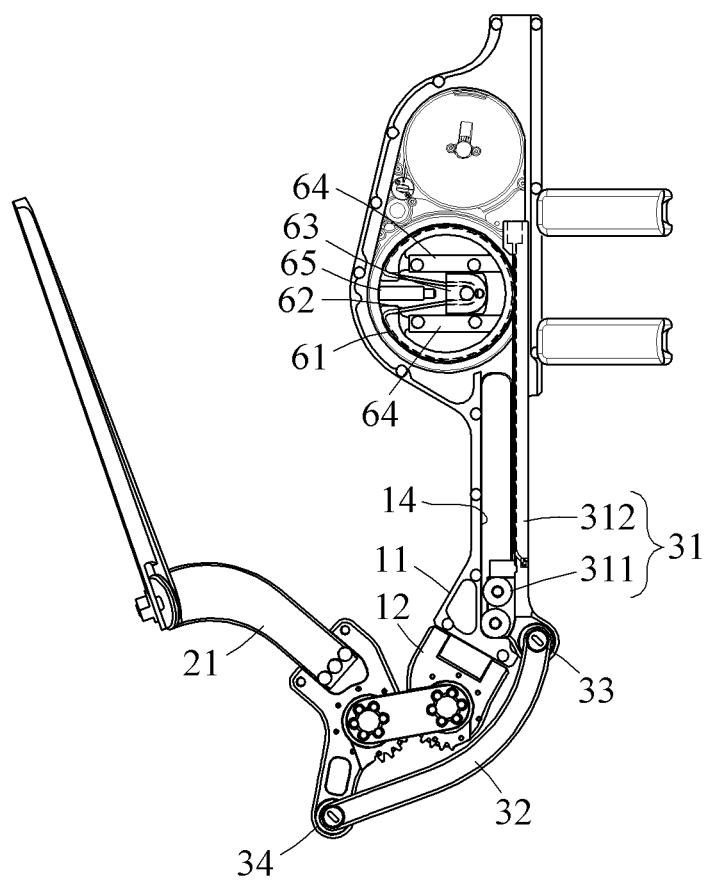
FIG. 8 is a right side view illustrating a motion assistance apparatus being in a flexion state according to at least one example embodiment.

FIG. 6 is a left side view illustrating the motion assistance apparatus being in an extension state according to at least one example embodiment, FIG. 7 is a right side view illustrating the motion assistance apparatus being in the extension state according to at least one example embodiment, and FIG. 8 is a right side view illustrating the motion assistance apparatus being in a flexion state according to at least one example embodiment.

Referring to FIGS. 6 through 8, the motion assistance apparatus 100 may include the proximal frame 10, the distal frame 20, the force transmitting member 30, the connecting member 40, the actuator 50, a rotary body 61, a wire 62, a tension adjusting piece 63, a piece guide 64, a piece adjustor 65, and a joint fixing member 70. The tension adjusting piece 63, the piece guide 64, and the piece adjustor 65 will be described in detail below with reference to FIGS. 9A through 9C.

The proximal frame 10 may include the first proximal segment frame 11, the second proximal segment frame 12, the first joint 13, the guide 14, and the proximal support frame 15. The distal frame 20 may include the first distal segment frame 21, the second distal segment frame 22, and the second joint 23. The force transmitting member 30 may transmit the power generated by the actuator 50 to the distal frame 20. The force transmitting member 30 may include the slider 31, the pusher 32, the first connector 33, and the second connector 34.

The rotary body 61 may be rotatably connected to one side of the proximal frame 10, and may rotate using the power generated by the actuator 50, thereby sliding the slider 31. For example, one end of the rotary body 61 may be connected directly to an output end of the actuator 50, or may be connected to the output end of the actuator 50 using a wire, a belt, or a gear train. The actuator 50 may be at a position closer to the proximal part of the user than the rotary body 61 is. The position may be, for example, an abdomen or a back of the user.

The wire 62 may connect the rotary body 61 and the slider 31. The slider 31 may include a first sliding part 311 configured to move along the guide 14, and a second sliding part 312 having a shape of a rod that extends and elongates from one side of the first sliding part 311. Both ends of the wire 62 may be fixed to both sides of the second sliding part 312, and a middle portion of the wire 62 may be wound over the rotary body 61 at least one time.

In the above connection structure, the slider 31 may move in both directions based on directions in which the rotary body 61 rotates. For example, when the rotary body 61 rotates in a clockwise direction, one end of the wire 62 may pull the slider 31 in a direction toward the distal frame 20 (e.g., in a downward direction). Conversely, when the rotary body 61 rotates in a counterclockwise direction, another end of the wire 62 may pull the slider 31 in a direction away from the distal frame 20 (e.g., in an upward direction). In the above structure, the power may be transmitted using a tensile force rather than a pushing force. Thus, although the rotary body 61 and the slider 31 are connected using the relatively flexible wire 26, instead of a rigid member, a bidirectional actuation of the knee joint of the user may be enabled without buckling.

Figure 10:
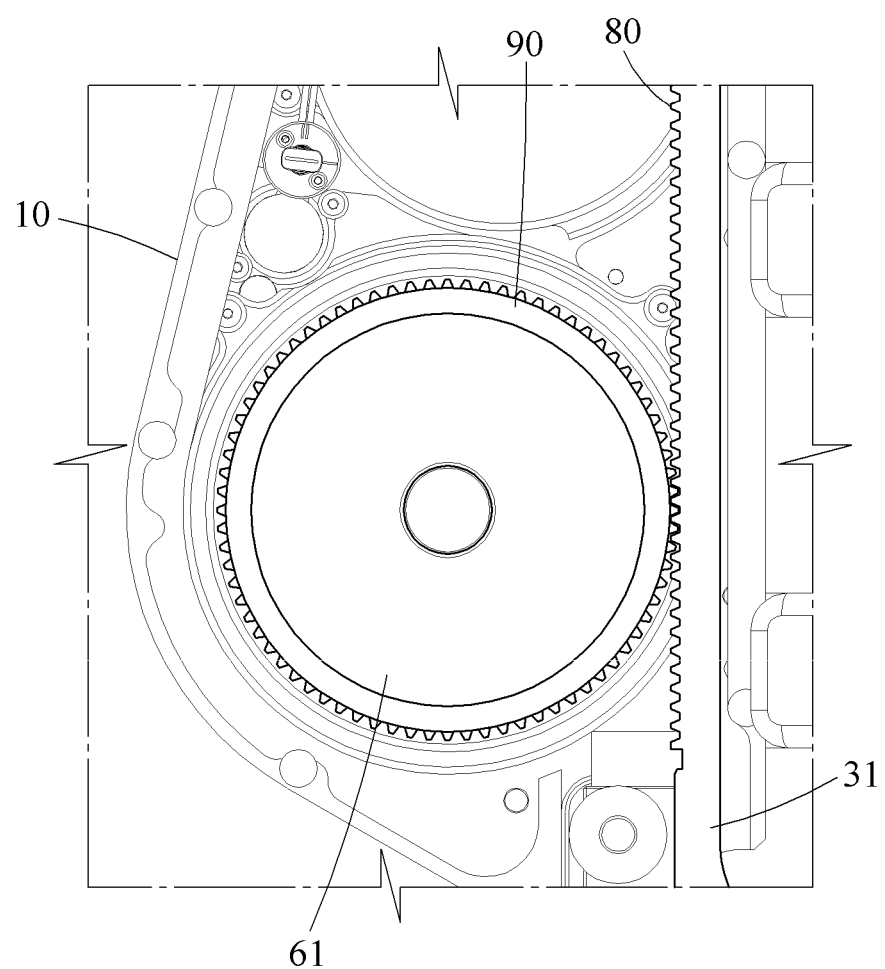
FIG. 10 is an enlarged portion of a right side view illustrating a rack gear and a pinion gear of a motion assistance apparatus according to at least one example embodiment.

Meanwhile, the above description is merely provided as an example. The rotary body 61 and the slider 31 may have any structure that may convert a rotational power generated by the actuator 50 to a rectilinear power. For example, as shown in FIG. 10, the wire 62 may be omitted, and the rotary body 61 and the slider 31 may have a pinion and rack structure.

The slider 31 may slide between a first position on the proximal frame 10 and a second position which is closer to the distal frame 20 than the first position is. For example, the first position may be a position of the slider 31 when the motion assistance apparatus 100 is in a full extension state, and the second position may be a position of the slider 31 when the motion assistance apparatus 100 is in a full flexion state. As the slider 31 moves from the first position to the second position, the angle between the slider 31 and the pusher 32 and an angle between the pusher 32 and the second distal segment frame 22 may decrease. In this example, the angle between the proximal frame 10 and the distal frame 20 may also decrease. Through the translational motion of the slider 31, the motion assistance apparatus 100 may assist a motion of a joint of the user.

The first sliding part 311 of the slider 31 may include a plurality of bearings. For example, two bearings may be on each of a left side and a right side of the first sliding part 311. The bearings may prevent tilting of the first sliding part 311 in a forward and backward direction and in a leftward and rightward direction. Thus, an unexpected space generated during a driving process of the 2-DOF motion assistance apparatus 100 may be reduced, whereby a stability and a control accuracy of the motion assistance apparatus 100 may improve.

The pusher 32 may have a curved shape. The pusher 32 may be a rod with a central portion curved to be convex in a direction from the proximal frame 10 toward a front side such that a distance from the proximal frame 10 may increase from both ends toward the central portion. The pusher 32 having the shape described above may be positioned close to the body of the user, and may be free from interference of the second proximal segment frame 12 and/or the second distal segment frame 22 while the proximal frame 10 and the distal frame 20 are in the full flexion state. Thus, a protruding height of the entire motion assistance apparatus 100 from the user may be reduced.

When the first proximal segment frame 11 and the second proximal segment frame 12 rotate on the first joint 13, the first connector 33 and the second connector 34 may enable a relative rotation between the slider 31 and the pusher 32. For example, while the user is switching a state of the knee joint from a flexion state to an extension state, the second proximal segment frame 12 may rotate outward with respect to the first proximal segment frame 11, and a portion of the pusher 32 connected to the second connector 34 may also rotate outward with respect to the slider 31. Conversely, while the user is switching the state of the knee joint from the extension state to the flexion state, the second proximal segment frame 12 may rotate inward with respect to the first proximal segment frame 11, and a portion of the pusher 32 connected to the second connector 34 may also rotate inward with respect to the slider 31.

The joint fixing member 70 may fix one of the first joint 13 and the second joint 23. For example, as shown in FIG. 6, the joint fixing member 70 may fix the second joint 23. When the joint fixing member 70 is released from the second joint 23, the first distal segment frame 21 and the second distal segment frame 22 may relatively rotate on the second joint 23. However, when fixed, the relative rotation between the first distal segment frame 21 and the second distal segment frame 22 may be restricted, and the first distal segment frame 21 and the second distal segment frame 22 may operate as a single frame. The user may dispose the distal frame 20 to be fully in close contact with a body, for example, the calf, while the joint fixing member 70 is released, and fix the joint fixing member 70 to reduce the protruding height of the motion assistance apparatus 100 from the body of the user.

Figure 9A:
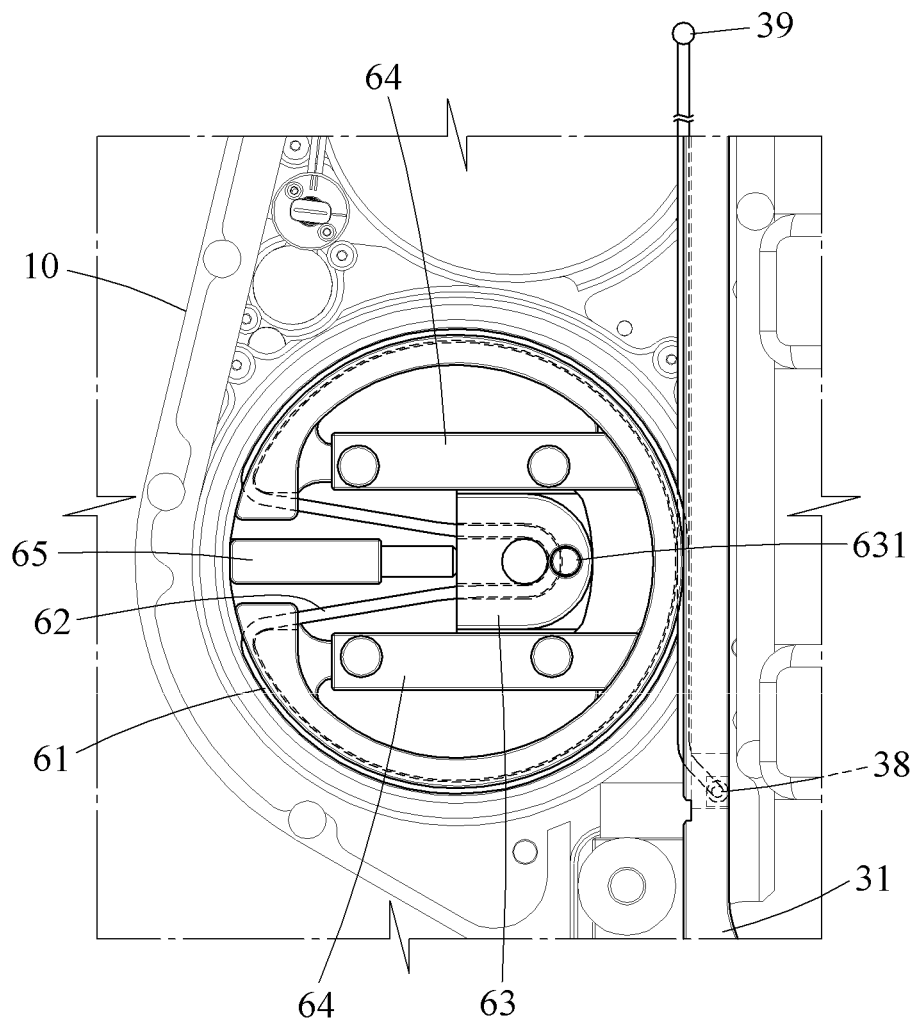
FIG. 9A is an enlarged portion of a right side view illustrating a rotary body, a wire, and a slider of a motion assistance apparatus according to at least one example embodiment.
Figure 9B:
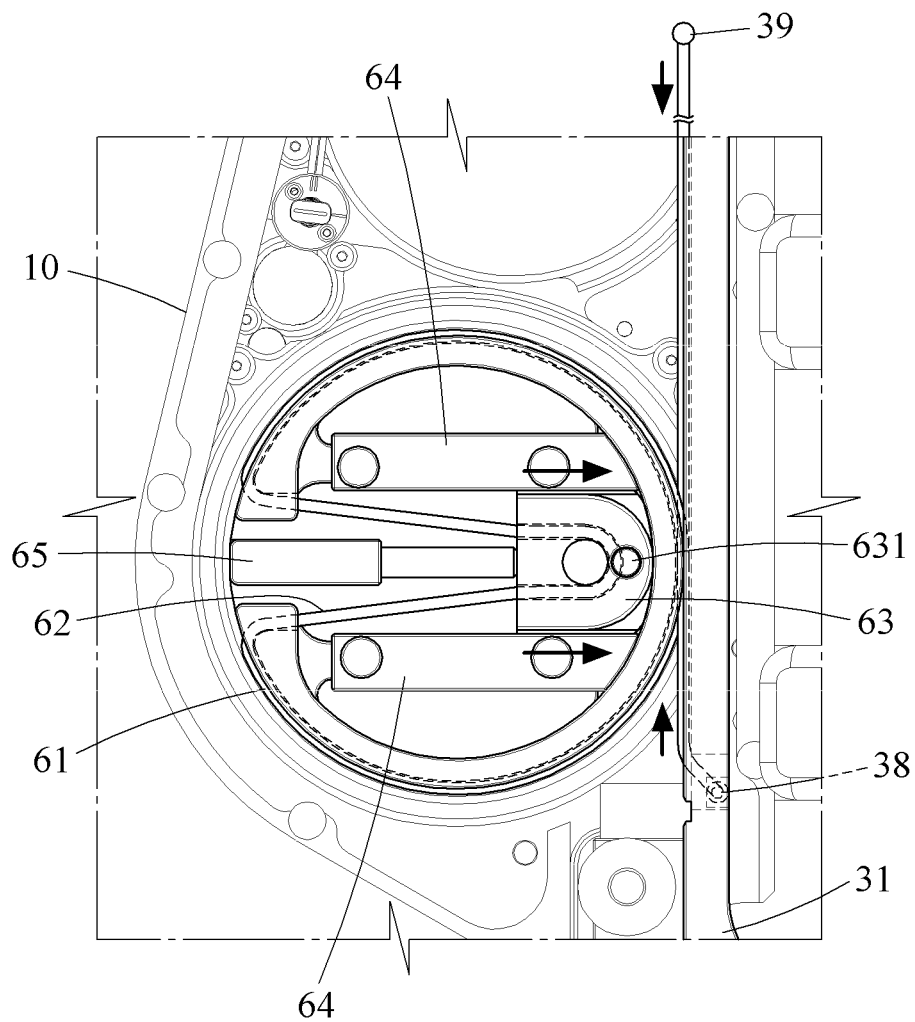
FIG. 9B is an enlarged portion of a right side view illustrating a mechanism for increasing an initial tensile force of a wire in a motion assistance apparatus according to at least one example embodiment.
Figure 9C:
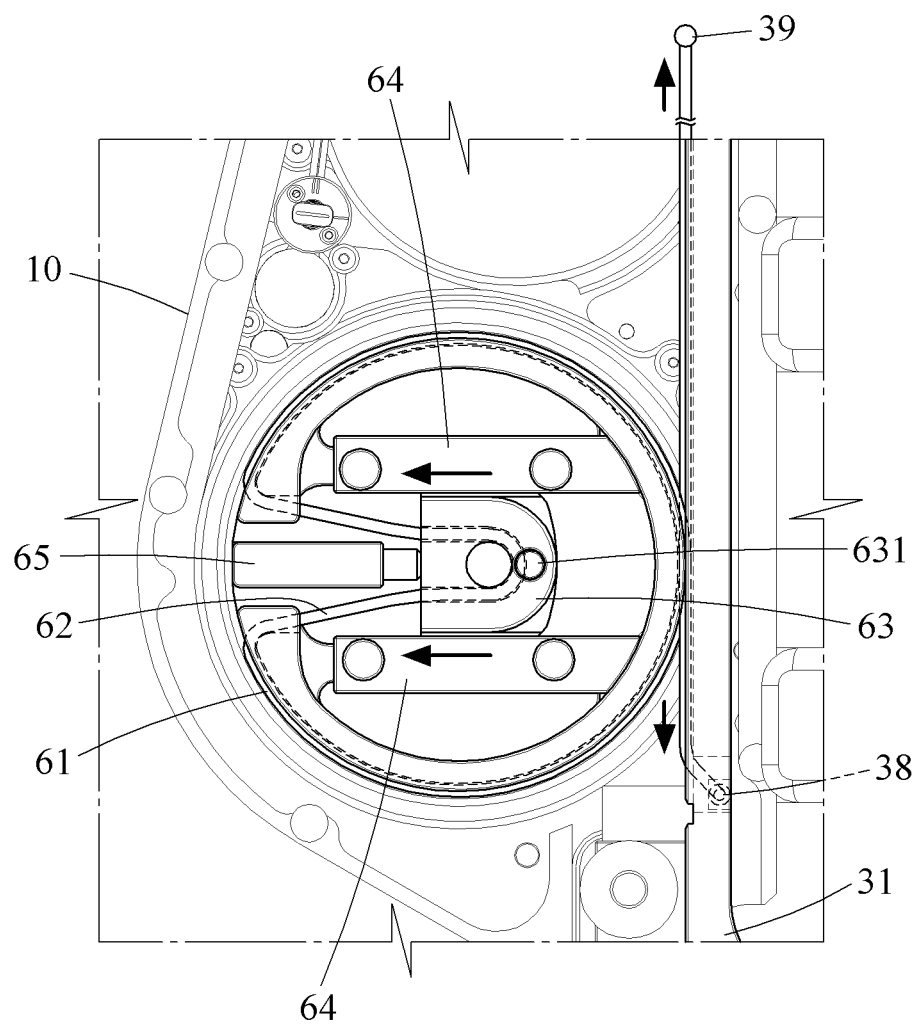
FIG. 9C is an enlarged portion of a right side view illustrating a mechanism for reducing an initial tensile force of a wire in a motion assistance apparatus according to at least one example embodiment.

FIG. 9A is an enlarged portion of a right side view illustrating a rotary body, a wire, and a slider of a motion assistance apparatus according to at least one example embodiment, FIG. 9B is an enlarged portion of a right side view illustrating a mechanism for increasing an initial tensile force of the wire in the motion assistance apparatus according to at least one example embodiment, and FIG. 9C is an enlarged portion of a right side view illustrating a mechanism for reducing an initial tensile force of the wire in the motion assistance apparatus according to at least one example embodiment.

Referring to FIGS. 9A through 9C, the rotary body 61 may be rotatably connected to one side of the proximal frame 10. The rotary body 61 may be connected to the output end of the actuator 50, and rotate using the power generated by the actuator 50.

The wire 62 may connect the rotary body 61 and the slider 31. Both ends of the wire 62 may be fixed to the slider 31. For example, one end of the wire 62 may be fixed to a first fixer 38 of the slider 31, and the other end of the wire 62 may be fixed to a second fixer 39 of the slider 31. The first fixer 38 and the second fixer 39 may be on opposite sides of the rotary body 61. A groove may be provided on each of a circumference of the rotary body 61 and a surface of the slider 31 to stably support the wire 62 and prevent a separation of the wire 62, and the wire 62 may be disposed along the provided groove.

The tension adjusting piece 63 may be movably connected to one side of the rotary body 61. The tension adjusting piece 63 may include a third fixer 631 to which the wire 62 is to be fixed, and may move to adjust a tensile force of the wire 62. As shown in FIG. 9B, when the tension adjusting piece 63 moves rightward, the tensile force of the wire 62 may increase. Conversely, as shown in FIG. 9C, when the tension adjusting piece 63 moves leftward, the tensile force of the wire 62 may decrease. When the tensile force of the wire 62 decreases due to aging as used for a long time, the user may increase the tensile force of the wire 62 using the tension adjusting piece 63.

The middle portion of the wire 62 may be wound over the rotary body 61 at least one time. For example, the wire 62 extending from the first fixer 38 may be wound along an upper circumference of the rotary body 61, inserted into the rotary body 61, and fixed to the third fixer 631. The wire 62 extending from the second fixer 39 may be wound over a lower circumference of the rotary body 61, inserted into the rotary body 61, and fixed to the third fixer 631. In this example, when the rotary body 61 rotates in a counterclockwise direction, the slider 31 may slide upward. When the rotary body 61 rotates in a clockwise direction, the slider 31 may slide downward. A position at which the wire 62 is fixed to the rotary body 61 may not be limited thereto. For example, the wire 62 may be fixed to a position on the circumference of the rotary body 61.

The piece guide 64 may be fixed to one side of the rotary body 61 to guide a movement of the tension adjusting piece 63. For example, the piece guide 64 may support both sides of the tension adjusting piece 63.

The piece adjustor 65 may adjust a position of the tension adjusting piece 63. For example, the piece adjustor 65 may include a bolt and a nut. The piece adjustor 65 may push the tension adjusting piece 63 in one direction using a change in a length of the bolt with respect to the nut, thereby increasing the tensile force of the wire 62.

FIG. 10 is an enlarged portion of a right side view illustrating a rack gear and a pinion gear of a motion assistance apparatus according to at least one example embodiment.

Referring to FIG. 10, the motion assistance apparatus 100 may include a pinion gear 90 rotatably installed in the proximal frame 10. For example, the rotary body 61 may include the pinion gear 90 along an outer circumferential surface thereof, and the slider 31 may include a rack gear 80 configured to engage with the pinion gear 90. In the above structure, when the pinion gear 90 rotates in a clockwise direction, the slider 31 may slide in a downward direction. When the pinion gear 90 rotates in a counterclockwise direction, the slider 31 may slide in an upward direction.

Figure 11A:
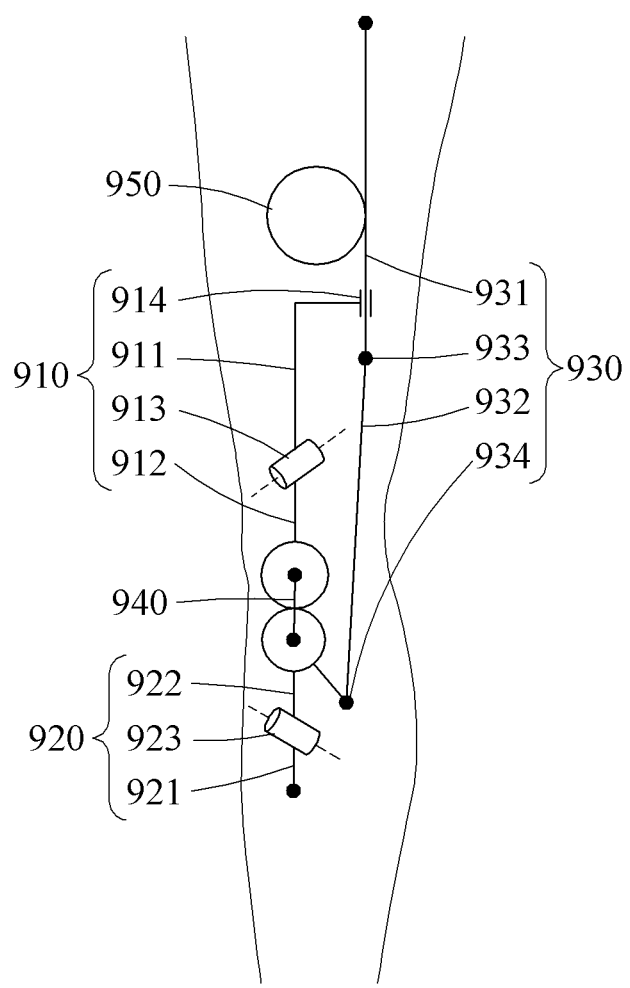
FIG. 11A illustrates a motion assistance apparatus being in an extension state according to at least one example embodiment.

FIG. 11A illustrates a motion assistance apparatus being in an extension state according to at least one example embodiment, and FIG. 11B illustrates the motion assistance apparatus being in a flexion state according to at least one example embodiment.

When compared to the example of FIGS. 3A and 3B, a motion assistance apparatus 900 of FIGS. 11A and 11B may include a force transmitting member 930 at a different position. In detail, when viewing a user wearing the motion assistance apparatus 900 from a side, the force transmitting member 930 may be positioned on a rear side from a central line of a thigh of the user.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus, comprising:
    a proximal frame configured to support a proximal part of a user;
    a distal frame configured to support a distal part of the user, the distal frame configured to rotate with respect to the proximal frame while remaining in a rolling contact with the proximal frame such that the distal frame is configured to perform a 2-degree of freedom (DOF) motion with respect to the proximal frame, the 2-DOF motion including a motion in a direction that traverses a sagittal plane of the user;
    a force transmitter slidably connected to the proximal frame, and rotatably connected to the distal frame; and
    a connector connected between the proximal frame and the distal frame such that the connector maintains the rolling contact between the distal frame and the proximal frame while the distal frame rotates with respect to the proximal frame.

2. The motion assistance apparatus of claim 1, wherein one or more of the proximal frame and the distal frame comprises:
    two segment frames; and
    a joint configured to connect the two segment frames such that a first one of the two segment frames rotates with respect to a second one of the two segment frames in a direction that traverses the sagittal plane of the user.

3. The motion assistance apparatus of claim 2, wherein
    the proximal frame includes two proximal segment frames, and a first joint configured to connect the two proximal segment frames, and
    the distal frame includes two distal segment frames, and a second joint configured to connect the two distal segment frames.

4. The motion assistance apparatus of claim 3, further comprising:
    a joint fixer configured to fix one of the first joint and the second joint such that the one of the first joint and the second joint is configured to switch between a first state in which the one of the first joint and the second joint is rotatable to allow the distal frame to rotate in the direction that traverses the sagittal plane of the user to place the distal frame in close contact with the user and a second state in which the one of the first joint and the second joint is fixed such that movement of the distal frame is restricted in the direction that traverses the sagittal plane.

5. The motion assistance apparatus of claim 2, wherein the joint is configured to have an axis that inclines such that the joint of the motion assistance apparatus is close to a joint of the user connecting the proximal part and the distal part of the user in a direction from a rear side of the user toward a front side of the user when the joint of the motion assistance apparatus fully extends.

6. The motion assistance apparatus of claim 1, wherein the proximal frame comprises:
    a guide configured to guide a movement of the force transmitter, the force transmitter including,
      a slider configured to move along the guide; and
      a pusher having a first end and a second end, the first end and the second end of the pusher rotatably connected to the slider and the distal frame, respectively.

7. The motion assistance apparatus of claim 6, wherein the force transmitter further comprises:
    a first connector configured to connect the slider and the pusher; and a second connector configured to connect the pusher and the distal frame, the first connector and the second connector each being one of a universal joint and a ball joint.

8. The motion assistance apparatus of claim 7, wherein the slider is configured to slide between a first position and a second position, the second position being closer to the distal frame than the first position such that an angle between the proximal frame and the distal frame decreases as the slider slides from the first position toward the second position.

9. The motion assistance apparatus of claim 8, wherein a shape of the pusher is convex in a direction away from the proximal frame when the proximal frame and the distal frame fully extend.

10. The motion assistance apparatus of claim 6, further comprising:
a rotary body rotatably connected to the proximal frame; and
a wire configured to connect the rotary body and the slider.

11. The motion assistance apparatus of claim 10, wherein first and second ends of the wire are fixed to first and second sides of the slider, respectively, and a middle portion of the wire is configured to wind over the rotary body at least one time.

12. The motion assistance apparatus of claim 11, further comprising:
a tension adjusting piece configured to move with respect to the rotary body, the tension adjusting piece having a portion of the wire fixed thereto.

13. The motion assistance apparatus of claim 6, further comprising:
a pinion gear rotatably connected to the proximal frame, and wherein
the slider includes a rack gear configured to engage with the pinion gear.

14. The motion assistance apparatus of claim 1, wherein the distal frame comprises:
a side frame connected to the proximal frame; and
a front frame configured to adjust a position thereof with respect to the side frame, and to enclose a front surface of the distal part.

15. A motion assistance apparatus, comprising:
a shank frame configured to support a shank of a user;
a thigh frame connected to the shank frame, the thigh frame configured to rotate in a first direction, the thigh frame including a joint, the shank frame configured to rotate with respect to the thigh frame while remaining in a rolling contact with the thigh frame, and the joint configured to rotate the shank frame in a second direction that traverses a sagittal plane of the user, the second direction differing from the first direction such that the thigh frame is configured to perform a 2-degree of freedom (DOF) motion with respect to the shank frame, the 2-DOF motion including a motion in the second direction that traverses the sagittal plane of the user;
a force transmitter slidably and rotatably connected to the thigh frame, and rotatably connected to the shank frame; and
a connector connected between the shank frame and the thigh frame such that the connector maintains the rolling contact between the shank frame and the thigh frame while the shank frame rotates with respect to the thigh frame.

16. The motion assistance apparatus of claim 15, wherein the joint of the thigh frame is above a knee of the user when the user is wearing the motion assistance apparatus.

17. The motion assistance apparatus of claim 15, wherein the shank frame comprises:
a joint below a knee of the user when the user is wearing the motion assistance apparatus, the joint of the shank frame being fixed and configured to deform the shank frame such that the shank frame is in close contact with the user.

18. The motion assistance apparatus of claim 15, wherein a rotation axis of the joint of the thigh frame inclines downward in a direction toward a front side of the user when the user is wearing the motion assistance apparatus.

19. The motion assistance apparatus of claim 18, wherein the joint of the thigh frame inclines downward at an angle, the angle being between 20 degrees and 70 degrees.

20. A motion assistance apparatus configured to assist a user, the motion assistance apparatus comprising:
a first frame;
a second frame configured to rotate with respect to the first frame while in a rolling contact with the first frame;
a connector connected between the first frame and the second frame such that the connector maintains the rolling contact between the second frame and the first frame while the second frame rotates with respect to the first frame, wherein
the first frame includes two first segment frames connected via a first joint, the first joint configured to act as a passive joint such that the first joint enables the second frame to rotate with respect to the first frame in a direction that traverses a sagittal plane of the user, and
the second frame includes two second segment frames connected via a second joint, the second joint configured to act as a fixed joint such that the second frame remains in alignment with a joint of the user while the user is walking; and
a rotary body and a force transmitter, the force transmitter including a slider, the rotary body and the slider configured to convert rotational power generated by an actuator to rectilinear power, and the force transmitter configured to transmit the rectilinear power to the second frame.

* * * * *